United States Patent
Otten et al.

(10) Patent No.: US 10,232,188 B2
(45) Date of Patent: Mar. 19, 2019

(54) SINGLE CABLE APPARATUS AND METHOD FOR HYPERTHERMIC TREATMENTS

(71) Applicant: Parmenides, Franklin, TN (US)

(72) Inventors: Thomas Otten, Indialantic, FL (US); George Clark, Indialantic, FL (US)

(73) Assignee: Thermofield Inc., Indialantic, FL (US)

( * ) Notice: Subject to any disclaimer, the term of this patent is extended or adjusted under 35 U.S.C. 154(b) by 163 days.

(21) Appl. No.: 15/383,510

(22) Filed: Dec. 19, 2016

(65) Prior Publication Data

US 2017/0143984 A1    May 25, 2017

Related U.S. Application Data

(63) Continuation-in-part of application No. 13/669,094, filed on Nov. 5, 2012, now Pat. No. 9,669,231.

(60) Provisional application No. 61/556,148, filed on Nov. 4, 2011, provisional application No. 62/269,948, filed on Dec. 19, 2015.

(51) Int. Cl.
*A61N 5/02* (2006.01)

(52) U.S. Cl.
CPC .................. *A61N 5/025* (2013.01)

(58) Field of Classification Search
CPC ...... A61N 1/403; A61N 5/025; A61N 5/0625; A61N 7/02
See application file for complete search history.

(56) References Cited

U.S. PATENT DOCUMENTS

| | | | |
|---|---|---|---|
| 6,216,703 B1* | 4/2001 | Manker | A61B 18/18 128/898 |
| 2004/0230263 A1 | 11/2004 | Samulski | |
| 2006/0142748 A1 | 6/2006 | Foreman et al. | |
| 2012/0065714 A1 | 3/2012 | Szasz et al. | |
| 2013/0237742 A1 | 9/2013 | Capstick et al. | |
| 2013/0241769 A1* | 9/2013 | Brannan | A61B 18/1815 342/372 |
| 2016/0074668 A1* | 3/2016 | Nunez | A61N 1/403 607/102 |

* cited by examiner

*Primary Examiner* — Thaddeus B Cox
(74) *Attorney, Agent, or Firm* — Cameron LLP

(57) ABSTRACT

A medical apparatus operable to induce localized hyperthermia in a patient via an electromagnetic field emitted by an antenna of an applicator connected to an output of the medical apparatus includes a signal generator, a bidirectional coupler, and a controller. The signal generator generates a radio frequency signal as a function of an operating parameter to a single cable to an applicator. The bidirectional coupler provides the radio frequency signal generated by the signal generator to the output and receives a reflected signal from the output at the applicator. First and second low pass filters isolate the radio frequency signal and reflected signal from a temperature sensing signal transmitted via the single cable to at least one temperature sensor of the applicator.

20 Claims, 5 Drawing Sheets

— SINGLE CABLE APPARATUS AND METHOD FOR HYPERTHERMIC TREATMENTS

CROSS-REFERENCES TO RELATED APPLICATIONS

This application claims the benefit of priority to U.S. Provisional Patent Application No. 62/269,948 filed Dec. 19, 2016 and is a continuation-in-part of U.S. patent application Ser. No. 13/669,094 filed Nov. 5, 2012, entitled "Apparatus and Method for Hyperthermic Treatments" of inventors Thomas Otten and George Clark, which application claims the benefit of priority to U.S. Provisional Application No. 61/556,148, filed Nov. 4, 2011, by George Clark and Thomas Otten, the contents of which applications being incorporated by reference in their entirety.

We, Thomas Otten and George Clark, citizens of the United States, residing at 507 South River Oaks Drive, Indialantic, Fla. 32903 and 445 Bahama Drive, Indialantic, Fla. 32903, respectively, have invented a new and useful "SINGLE CABLE APPARATUS AND METHOD FOR HYPERTHERMIC TREATMENTS".

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

BACKGROUND

The present invention relates generally to apparatus, systems, and methods for the hyperthermic treatment of patients which can include the co-administration of various pharmaceuticals to the patient. In optional embodiments of the invention, different applicator and antenna designs may be utilized to provide for radiation with different radio frequency signal operating parameters so as to be best applicable to various anatomical sites for various patients. The invention may also include set procedures as well as software for using the applicator to treat a patient.

A first embodiment will be discussed comprising a two cable design followed by a disclosure of a second embodiment comprising a single cable design in which embodiment the two cables are replaced by a single cable and alternative electronic circuits to improve, for example, the measurement of incident radio frequency power to reflected power, i.e., delivery of power and hypothermic treatment to a patient and the measurement of temperature at a position of treatment for regulating transmitted radio frequency power.

Hyperthermic therapy is understood to be the exposure of a patient to a higher temperature than their own body temperature. Oftentimes hyperthermia is used as a type of cancer treatment with temperatures of bodily tissue easily exceeding 110° F. or higher than 39° C. or, for example, at least 42° C. It is known in the art that higher temperatures can often damage tumor cells including cancer cells while leaving normal tissue cells unharmed. Such application may either shrink or remove tumors from a patient and in some instances may be combined with other treatment options such as immunotherapy and chemotherapy and/or radiation to create a synergistic effect in treating the patient. A variety of different cancers may be treated with hyperthermic devices, a sample of which may include brain cancer, lung cancer, melanoma as well as additional other types.

In some hyperthermic treatments, heat may be applied in a localized area which may include the use of microwaves, ultrasound or various types of radiation. Some approaches are external wherein a device is positioned near the desired area for treatment and heating is facilitated. In other styles of treatment, the treatment methods may be described as internal where a probe may be placed within body cavities or alternatively inserted into the tumor directly with heat subsequently applied. In yet further types of hyperthermic treatment, certain treatment styles may include treatment for the entire body which can include placing the patient within a chamber that may raise the body temperature significantly.

A common concern with hyperthermia treatment is the potential discomfort from burns, swelling or other side effects resulting from the heating of an area of a patient's body. A variety of various prior art methods may utilize cooling systems so as to reduce the surface temperature of the skin while still heating the underlying tissue. Unfortunately, such arrangements can be very difficult to coordinate the desired frequency with the desired heating of a tumor and can affect heating depth.

Samulski, U. S. Patent App. Pub. No. 2012/0230263 published Nov. 18, 2004, describes a non-invasive apparatus and method for providing RF energy-induced localized hyperthermia. Samulski has a concave profile applicator body in which tissue (such as a breast or chest wall) may be immersed.

Samson et al., U.S. Patent App. Pub. No. 2005/0004503 published Jan. 6, 2005, (Samson) describes a method and apparatus for treating acute myocardial infarction with hypothermic perfusion. Samson discloses coronary artery perfusion catheters and may include guidewires, subselective catheters and/or interventional catheters introduced through a lumen.

Foreman et al., U.S. Patent App. Pub. No. 2006/0142748 published Jun. 29, 2006, (Foreman) describes devices for targeted delivery of thermotherapy, and methods related thereto. Foreman suggests administration of a thermotherapeutic magnetic composition to a patient or portion of a patient and the application of an alternating magnetic field to inductively heat the composition.

Szasz et al., U. S. Patent Appl. Pub. No. 2012/0065714 published Mar. 15, 2012, (Szasz) describes a radiofrequency hypothermia device with target feedback signal modulation. A sensor receives a feedback signal from a target to a feedback amplifier and modulates the source signal to generate a target modified signal, thus, allegedly, increasing the selectivity of the hypothermia treatment.

While hyperthermia technology has been used for a variety of patients, these previous hyperthermia technologies suffer from limitations including significant side effects to the patient as well as unpredictability of the heating pattern of a patient and limited depth of heating pattern. Additional complications may arise from the possible inadvertent administration of heat and/or electromagnetic radiation to the medical care provider. What is needed, therefore, is an apparatus, method and system of providing hyperthermic treatment to a patient which may be administered for a localized region while being predictable, controllable and easy to monitor so that less energy is used and the chances of side effects are minimized.

SUMMARY OF THE ALTERNATIVE EMBODIMENTS

The present invention relates generally to an apparatus, system and method for administering hyperthermia treatment to a patient utilizing, in one embodiment, first and second cables and, in a further embodiment, a single cable providing the features of the first and second cable design and additional features. In optional embodiments of the apparatus, the device may be a medical apparatus operable to determine the delivery efficiency of electromagnetic radiation to a patient by measuring the efficiency of delivery in comparison with measured temperature at the treatment site and so regulating the efficiency so as to not endanger the patient.

In one aspect of the invention, a medical apparatus is operable to induce localized hyperthermia in a patient via an electromagnetic field emitted by an antenna connected to an output of the medical apparatus. The medical apparatus includes a signal generator, a bidirectional coupler, and a controller (which may be located near a patient, for example, within approximately four feet). The signal generator is operable to generate radio frequency signal as a function of an operating parameter. The bidirectional coupler is connected to the signal generator into the output of the medical apparatus. The bidirectional coupler is operable to provide the radio frequency signal generated by the signal generator to the output and to receive a reflected signal from the output, for example, when the impedance of the patient does not match the impedance of an applicator device containing the antenna (for use in hypothermic treatment of the patient and so adapted to be flexible and be placed on a treatment site of the patient). The controller is connected to the bidirectional coupler into the signal generator. The controller is operable to receive the generated radio frequency signal from the generator, determine a power of the radiofrequency signal generated by the signal generator, receive the reflected radio frequency signal from the bidirectional coupler, determine a power of the reflected signal, and to terminate delivery efficiency of the medical apparatus as a function of the power of the radiofrequency signal generated by the signal generator and the power of the reflected signal received from the bidirectional coupler when the efficiency falls below a predetermined level. A technician may then attempt an alternate positioning of the applicator on the patient near the treatment site in order to increase impedance matching, decrease reflected radio frequency power and more effectively deliver heat at the treatment site measured by at least one temperature sensor of the applicator at the treatment site. Optionally, the medical apparatus may vary the operating parameter, determine the operating parameter variation that provides optimal delivery efficiency, and operate at the determined operating parameter providing optimal delivery efficiency.

In another aspect of the invention, a method of inducing localized hyperthermia in a patient via an electromagnetic field emitted by an antenna connected to an output of a medical apparatus includes generating a radiofrequency signal via a signal generator of the medical apparatus. The radiofrequency signal generated by the signal generator is provided to the output of the medical apparatus via a bidirectional coupler of the medical apparatus. A reflected signal is received from the output at the bidirectional coupler. The generated radiofrequency signal from the signal generator is received at a controller of the medical apparatus. The controller determines the power of the radiofrequency signal generated by the signal generator. The reflected signal is received at the controller from the bidirectional coupler. The controller determines a power of the reflected signal. The controller then determines a delivery efficiency of the medical apparatus (in particular, the applicator at the treatment site) as a function of the power of the radiofrequency signal generated by the signal generator and the power of the reflected signal received at the processor from the bidirectional coupler.

In additional optional embodiments of the invention, the applicator may be designed for a specific frequency so that the applicator can be tailored to provide heat at a specified depth within a patient. More particularly, the applicator optionally may be anatomically designed to fit a specific size and location of a patient so that optimal contact of the applicator to the individual's skin is achieved and delivery of treatment optimized. More particularly, optional embodiments of the applicator may include an applicator that operates at 434 MHz or alternatively an applicator that operates at 915 MHz as both frequencies have proven to be useful in administering electromagnetic radiation to individuals for the purpose of hyperthermia treatment. Other frequencies may be used for differing depths of treatments in a range, for example, between 400 MHz and 1 GHz.

Additional optional embodiments may include the use of software to control a pulsing or constant application of electromagnetic radiation to an individual for the purpose of hyperthermic treatment. Therefore, there may be software designed for the controller to allow one to make the necessary choices in administering the treatment as desired by the health care provider to the individual needing hyperthermic treatment.

An optional aspect of the present invention is to provide an applicator for hyperthermia treatment that may be used in direct contact with the patient's skin for providing heat and is flexible for contacting differently shaped treatment sites such as breasts, necks, abdominal regions, backs and extremities.

Another optional aspect of the invention is an applicator that provides a specific frequency so that penetration to a specific depth within the patient is known to match and intended treatment site such as skin depth to several centimeters.

Yet another optional aspect of the invention is an applicator for administering electromagnetic radiation that is sized and adapted for use at specific anatomical locations on a patient.

Yet a further optional aspect of the invention is a method of treating various ailments ranging from muscular issues to cancer.

Still a further optional aspect of the invention is a system including the use of electromagnetic radiation to raise the temperature of a localized region of a patient while simultaneously administering a drug to the patient (for example, chemotherapy or immunotherapy) so that a synergistic effect is achieved at the site of the electromagnetic radiation.

In accordance with the purpose of the invention, as embodied and described herein, the invention in optional embodiments may include an applicator for administering electromagnetic radiation at a desired frequency to a patient having an ailment which may be treated through hyperthermia. The invention may be utilized with patients ranging from various types of animals including horses, cats and dogs to humans as well.

The applicator of further optional embodiments may incorporate a variety of different designs so as to be used for various locations on or in the patient's body. As used herein, the term "patient" means any animal as well as human that may benefit from a hyperthermia treatment. While some patients may have physical ailments such as cancer, it is conceivable that other patients may only have simple aches and pains which may also benefit from the administration of hyperthermic treatment through the use of the invention as described herein.

The accompanying drawings are incorporated in and constitute part of the specification. The drawings illustrate optional embodiments of the invention and together with the description serve to explain some principles of the invention.

BRIEF DESCRIPTION OF THE SEVERAL VIEWS OF THE DRAWINGS

Embodiments of a two cable hypothermia system are described by FIGS. 1 and 2 and alternative embodiments of a single cable system are described by FIGS. 3, 4 and 5.

FIG. 4 shows a plurality of ferrite beads 402 through 405 which block radio frequency from the one wire temperature sensor 308 so that the high power radio frequency signal may proceed directly to antenna 410 and any reflected radio frequency signal is also blocked from passing through the low pass filter to reach one wire temperature sensor 308. The sample and hold circuit may comprise a diode 407, a resistor 408, a large capacitor 409 for retaining a charge (for example, to sustain a low frequency temperature data polling rate of about one temperature value per second and provide voltage Vdd to the temperature sensor 308.

Further details of an improved single cable system will become apparent from the following detailed description of the preferred embodiments.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of the embodiments described herein, a number of terms are defined below. The terms defined herein have meanings as commonly understood by a person of ordinary skill in the areas relevant to the present invention. Terms such as "a," "an," and "the" are not intended to refer to only a singular entity, but rather include the general class of which a specific example may be used for illustration. The terminology herein is used to describe specific embodiments of the invention, but their usage does not delimit the invention, except as set forth in the claims.

Terms such as "providing," "processing," "supplying," "determining," "titrating," or the like may refer to an action of a computer system, computer program, processor, logic or alternative analog or digital electronic device that may be transformative of signals represented as physical quantities, whether automatically or manually initiated. As used herein, a "bidirectional coupler" may refer to a duplexer, a circulator, or any other component enabling duplex communication or signal transmission in a single medium.

Figure 1:
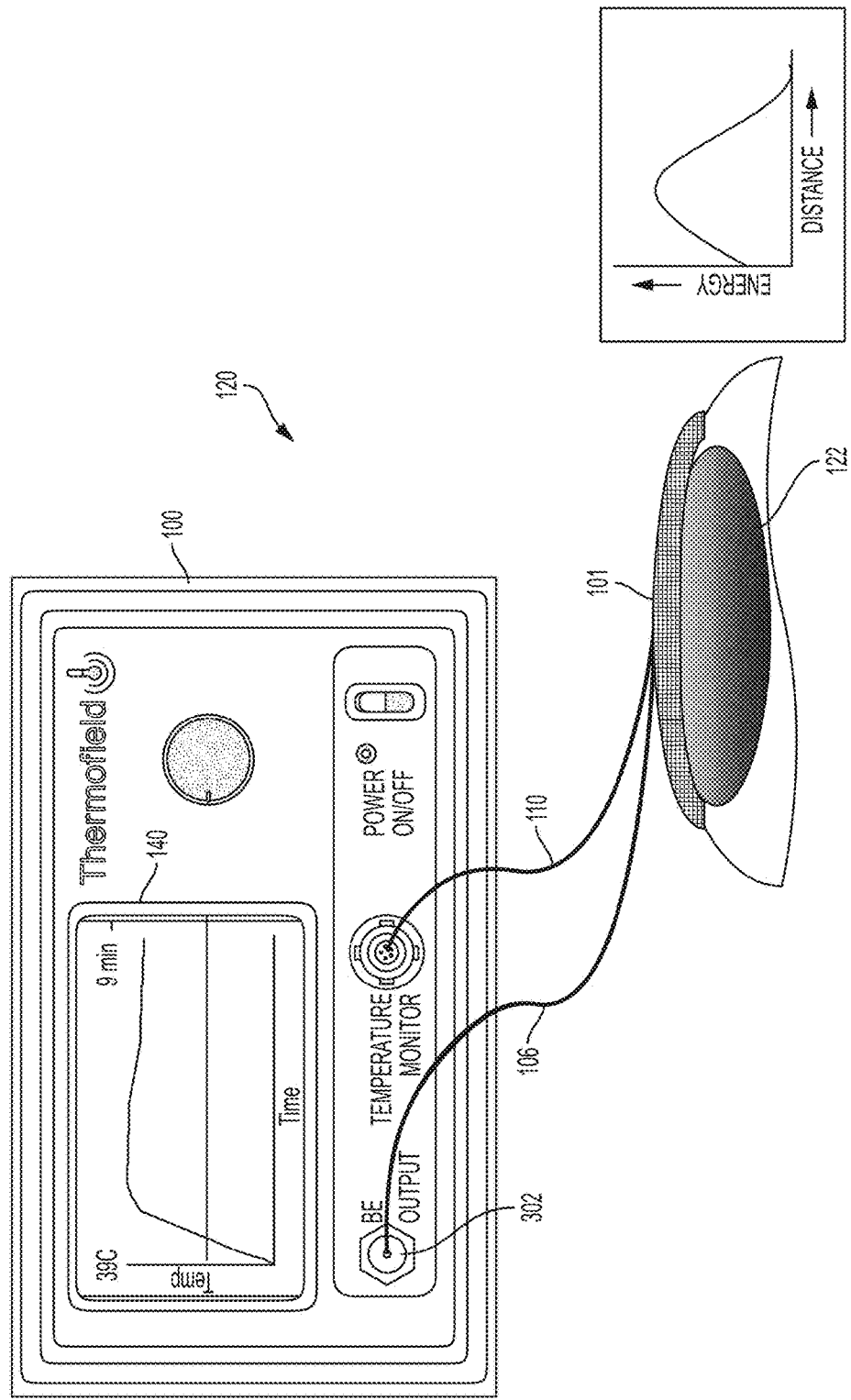
FIG. 1 is a block diagram of a two cable Thermofield system including a display, a controller (not shown) and first and second cables wherein cable 106 connects a radio frequency output/reflected input to an applicator 101 having an antenna and cable 110 connects to at least one temperature sensor for assisting in regulating the delivered radio frequency signal to a treatment site for delivering a hypothermia treatment 122 at the juncture of a patient treatment site and the applicator 101. Electromagnetic radiation may raise the temperature of a localized region of a patient, for example, while simultaneously administering a drug to the patient so that a synergistic effect is achieved at the site of the electromagnetic radiation.

Referring now to the figures, FIG. 1 is a block schematic illustration of a control unit 100 and an applicator 101 of the present invention (two cable system). As is illustrated, there may be a variety of different layers in forming the applicator 101 for administering electromagnetic radiation to a patient. Generally, the antenna portion of the application for delivery of electromagnetic energy to a treatment site via first cable 106 comprises the major portion of the applicator 101 and is the portion responsible for creating the electromagnetic field for inducing localized hyperthermia in the patient. A temperature monitor and second cable 110 may assist in regulating delivery of electromagnetic energy. In optional embodiments of the antenna, the antenna may have dimensions of about 11 cm×15 cm×1.5 cm as such size may work with a variety of different anatomical locations on a patient's body. The layer in contact with the skin, the lowest layer of the design, is generally understood to be a high impedance substrate. Generally the high impedance substrate can be understood as being an insulating layer and can be formed from a piece of flexible silicone. While other materials may be used as a high impedance substrate, the use of flexible silicone can possibly be advantageous as it allows a flex of the antenna so that the antenna may be in greater physical contact with the surface of the patient and match impedance with the patient to reduce reflection then if the high impedance substrate was rigid and would not allow for flex of the antenna.

A next layer of the applicator can be understood to be the slot antenna (further described in parent patent application, U.S. Ser. No. 13/669,094 filed Nov. 5, 2012, incorporated by reference as to its entire contents). Generally, the layer that forms a slot antenna may be understood to be formed of a metallic material which may optionally be copper on top of a printed circuit board (PCB). In optional embodiments, the PCB is also flexible so as to allow for conformal application to a variety of anatomical sites. As used herein, the term "slot antenna" generally describes the use of a metal material, usually in a flat arrangement, with either a whole slot or opening cut away. Slot antennas function similarly to dipole antennas in that when driven by a specific frequency the slot radiates electromagnetic waves based on the configuration of the slot as well as the frequency, both determining the distribution pattern of the radiation. Additionally, the length and width of the slot within the antenna can determine the impedance of the slot antenna. In optional embodiments of the invention, the aperture in the slot antenna may measure approximately 35 cm$^2$ to about 45 cm$^2$ and in further optional embodiments may measure about 35.9 cm$^2$. In forming the applicator 101, an additional layer of a high impedance substrate may be placed above the slot antenna with a feed line 106 being there on top. In optional embodiments, the microstrip feed line 106 is also fabricated using a PCB and can be used to help convey radiofrequency and/or microwave frequency signals. In additional optional embodiments, the microstrip feed line 106 may be a 50 ohm microstrip feed line. An additional high impedance substrate layer may be positioned on top of the feed line 106 layer with all layers combined together to provide for a flexible applicator 101. An additional shielding layer may be on top of the top layer of the high impedance substrate which may provide shielding qualities so that electromagnetic radiation is directed toward the patient and blocks from a mission toward a caregiver (e.g., veterinarian, doctor, nurse or other skilled medical technician) or user of the medical apparatus and applicator 101.

In further optional embodiments the applicator may additionally include a thermosensor (i.e., temperature sensor, 102, FIG. 2) incorporated into the applicator 101 to allow for treatment, monitoring and control while administering heat to a patient. Through use of the thermosensor which may be integrated into the device, a provider can understand and realize the surface temperature of the patient's skin adjacent the applicator 101 and thus adjust the medical apparatus accordingly if discomfort or other issues are noted. While a temperature sensor cable 110 is shown, it will be described herein that connector cable 106 is preferably integral with temperature sensor cable 110 and provides power to a one wire temperature sensor as will be discussed herein as well as collect temperature data. In alternative embodiments, more than one temperature sensor may be utilized such as three temperature sensors built into the applicator 101 and uniquely identified for example by a two bit code when polled or reporting temperature results. One such temperature sensor may be embedded (injected) at the tumor site to directly measure the temperature at the tumor.

Notice the graph of energy versus distance in FIG. 1, where it may be seen that the longer the distance that electromagnetic energy has to travel the electromagnetic energy reaches a peak and then degrades to no energy as distance increases. It is appropriate to have a dual (or single cable in the embodiments of FIGS. 3-5) cable system that is short enough to deliver maximum energy at the top of the energy/distance curve. This top is for typical radio frequency cables reached for the frequencies considered of 0.4 GHz to 1 GHz about two to six feet or preferably about four feet so that the control unit should be about four feet from the patient and treatment site.

In additional optional embodiments of the applicator 101, the applicator 101 may include a stiffener within the applicator so that the applicator maintains a rigid formation. Optional embodiments of this design may include a polyimide stiffener as the middle layer so as to provide stiffness to the applicator 101. There may be a variable thickness of the applicator design showing the layers in contact with one another as to how the device would be used when applied to patients in certain optional embodiments. The applicator 101 thus may have a thickness somewhere between about 0.3 inches to about 0.4 inches and in other optional embodiments may include a thickness of about 0.32 to about 0.37 inches. This applicator in optional embodiments may also include a cover coating to combine all the layers and hold the layers together while protecting aspects of the applicator 101. The cover coating may range from about 0.02 to about 0.08 inches thick and in further optional embodiments may comprise a covering of about 0.04 inches thick.

A top laminate of the applicator 101 including a microstrip having inputs for various devices. Optional embodiments may include a radio frequency (RF) connector with the connector being connected to the top side of the laminate so as to provide the necessary connection for the connector cable 106 to the output of the medical apparatus. The second connector is in optional embodiments attached to the bottom laminate with the antenna and can provide a connection to the temperature sensor. It has been found that in a two cable design, some radio frequency power leaks between cable 106 and cable 110 such that the measurement of the efficiency of the applicator with respect to the patient is impaired. Moreover, the first and second cables 106 and 110 may become entangled with one another impeding operation.

Generally, applicator access may be provided through the top laminate via a cut out which may allow the top laminate unrestricted motion at this point and help avoid situations where the laminate may buckle. In yet further optional embodiments, the second connector may be a quick disconnect miniature stereo jack which may prevent interconnect failure due to solder fraction if the cable is yanked.

The bottom laminate having the antenna may further provide optional arrangements for the gap width. There may be a 0.565 gap width for this configuration. Generally, the slot antenna may be separated from the microstrip feed line by a silicone pad which is generally of from about 0.04 inches thick to about 0.08 inches thick and in optional embodiments may be about 0.062 inches thick. As previously discussed, both the top and bottom silicone pad may be the same thickness. They can serve to cushion the top and bottom laminates from outside impact as well as cover protrusions from the connectors at the top and also cover the protrusion resulting from the one or more temperature sensors 102 (for example, in a triangular pattern) that in optional embodiments may be attached to the bottom of the bottom laminate.

Generally the laminates are described as flexible and the laminates may be understood to have various thicknesses though in optional embodiments may be about 0.004 inches thick. A connector cables 106 and a temperature sensor cables 110 may be used with the invention with cable lengths running anywhere from a couple feet to multiple feet in length to allow applicator 101 operation and evaluation at greater distances so as to be convenient for the health care provider and the patient. In a preferred embodiment per FIGS. 3-5, the connector cable and temperature sensor cables are combined into one cable to maximize efficiency readings of delivered power to a patient and so regulate power delivery according to temperature at the treatment site.

In further optional embodiments the antenna of the applicator 101 may take on various configurations especially when situated with the feed line 106. The radio frequency antenna may typically operate at about 434 MHz (e.g., 400 to 460 MHz). Generally dimensions for this type of antenna have been found to be useful at about 150 mm by about 110 mm though in further optional embodiments this may be larger or smaller. Generally this antenna is utilized with a radio frequency transceiver operating at about 434 MHz (e.g., 400 to 460 MHz) which optionally may have a variable power output. The transmitted (or intended incident power delivered to the treatment site) for such systems of this invention may vary anywhere from about 5 watts to about 40 watts though in other optional embodiments may vary from about 5 watts to about 20 watts depending upon the application intended patient type. In tailoring the invention for treatment of patients and the necessary interaction of electromagnetic fields with tissue, variables should be defined to determine delivery effectiveness (efficiency) of the device including applicator 101. One such parameter includes a specific absorption rate which generally provides estimates of the total real power that is transmitted into the tissue at a treatment site. Additionally return loss is generally understood to reflect the measurement of reflected energy as a result of the mismatch between the applicator and the tissue impedance. Ideally, matching of impedances is achieved so that reflected power is minimized and all transmitted power is delivered to the treatment site. Through the use of these variables, one is able to determine the efficiency (i.e., delivery efficiency) of energy transferred for different applicator 101 locations, antenna configurations (i.e., feed strip line and slot antenna sizes, shapes, and spatial relationships), and operating parameters of a radio frequency signal driving the applicator 101 in dealing with patients.

Simulations have demonstrated matching the measured values best at about 434 MHz (i.e., 400 to 460 MHz) with acceptable tissue/applicator impedance matching between tissue and the applicator 101 being defined as return loss of less than about 10 decibels. In examining and testing the applicator 101 having the configuration as described above, measurements can be made in connection with various anatomical locations for a variety of patient species to determine optimal applicator designs (i.e., size, shape, and spatial relation of the feed line 106 and slot antenna) and the frequency, duty cycle, pulses per second, and power level of the radiofrequency signal driving the applicator 101.

Specific absorption rate versus distance from the surface of the tissue for the applicator 101 ha been measured driven by a radiofrequency signal at 434 MHz. The further the antenna is from the tissue, the lesser absorption of electromagnetic field there is by the patient with there being a significant drop once the distance is greater than about 10 mm from the surface of the tissue.

Measurements of the antenna illustrating the lowest return loss at 434 MHz using an absorber have been made and the same effectiveness was found with the general shape very closely nearing that of the antenna alone. Alternatively, the positioning of a user's hand, generally the health care practitioner, significantly shifted the frequency by both the antenna and hand line and the antenna, hand, and absorber line. The antennae simulation generally tracked the frequency response of the measured antenna and the antenna with the absorber. As such, a simple absorber may not be a significantly useful material because a hand on the back side of the applicator 101 significantly altered the electromagnetic field as intended to flow within the localized area of the patient.

A near field representation for the antenna of the present invention in the x-z plane when the applicator 101 is above tissue and energized at approximately 434 MHz was performed. This optional embodiment of the antenna configuration provides a relatively uniform electromagnetic field across the length of the antenna and penetrates fairly deep within the soft tissue boundary while exhibiting a lesser effect on the skin's surface. The antenna may include a shield which improves the directivity and substantially reduces back field radiation. Otherwise stated, the addition of a floating shield plate above the antenna (i.e., slot antenna and feed line 106) eliminates to a significant degree the back field irradiation.

A representation of the electromagnetic field at about a 1 cm depth in the local area of the patient was performed. Additionally, simulations for calculating a specific absorption rate show that the antenna design of this embodiment may have a tissue penetration depth of over 4 cm and generally may be about 4.59 cm (about two inches) though in other optional embodiments, the tissue penetration depth may differ.

Further optional embodiments of portions of the applicator 101 may be used for the present invention with the antenna (i.e., slot antenna and feed strip) having a half size of the antenna (i.e., slot antenna and feed strip). In such optional embodiments, this antenna (i.e., slot antenna and feed strip) may have dimensions of approximately 75 mm by 110 mm. Advantages that may be present from the half size designs may be the ability to place the half size applicators at anatomical locations where the larger size applicators and antennas would not fit. As previously described, the applicator performs best when in contact with the skin. (With no contact, reflected power increases and no heat is delivered to a treatment site). With the half size configuration, certain locations can be better managed and thus better treatment can occur. Other optional embodiments for the applicator design may include designs which illustrate different configurations of the antenna (i.e., slot antenna and feet strip) as the gap between the two small patches is removed. This is best illustrated in FIG. 12A. Return losses may vary depending on antenna and applicator design between about −17 dB at 434 MHz compared to about −32.29 dB as measured for other antenna designs and applications.

There are additionally other types of antennas that may be utilized and applicant is not limited through his disclosure to any of the designs but rather intends to provide these examples to show how various antennas can be used with applicant's invention. For example, there may be different antenna designs which generally can include dimensions of about 98 mm to about 110 mm.

Optional embodiments of the invention may include other frequencies and may be used to generally include the same component parts that may be used with or without a shield on the top surface. Two wavelengths that have been used in various optional embodiments of the present invention include 434 MHz and 915 MHz though other frequencies may be selected and utilized. Generally these frequencies pair best with the animal tissue (i.e., the local area of the patient adjacent the applicator or antenna) with the specific antenna design as described here within the application.

For various applications where the applicator 101 may not be in direct contact with the patient's body, the frequency of the radiofrequency signal driving the applicator 101 may have to be adjusted so that proper penetration with the tissue is achieved. In such embodiments of the invention, the high impedance substrates are interspaced between the microstrip feed line and the antenna with a shield typically on the outermost high impedance substrate. The invention may include a coupler for connection to provide for connection with a radiofrequency transceiver. Other connections of the applicator 101 may be for a temperature sensor or probe which can measure the surface temperature of the user's skin.

The applicator 101 of the present invention includes a variety of traits, one of which may optionally be having a flexible construction such as to better match applicator to patient treatment surface. As the surfaces of patients are rarely completely flat, the flexible construction allows for the applicator 101 to be in direct contact with the patient and thus provide for the effective transfer of electromagnetic energy to the patient (and minimize reflected power). Advantageously, the invention may include optional embodiments with the feed line in a central position and fixed relative to the slot antenna to maintain a location with respect to the other layers of the antenna to provide for field consistency.

In one embodiment, the high impedance substrate and optional embodiments have a dielectromagnetic constant between about 2.5 and 3.5 which may be selected based upon the specific tissue composition for which treatment is sought. Most often the substrate is a silicone polymer which can be varied based upon a species and the anatomical site to be treated.

The invention of this application allows a user to test the permitivities for different species and locations on different species and thus optimize construction of the antenna with the specifically desired dielectromagnetic constant of the substrate material that provides for the best performance. In embodiments, the system as a whole can detect reflected power while in use so a user can reposition the antenna and applicator to optimize a radio frequency signal driving the antenna to maximize energy delivery to the patient. Various options exist for controls for the invention with systems ranging from a simple on or off of the radiofrequency signal driving the antenna operating at a set frequency and power level to a series of pulses (i.e., pulse width modulated) or otherwise pre-specified arrangements. In optional embodiments, radiofrequency pulses may be about one millisecond in length at a desired frequency with a user able to vary parameters to achieve an in vivo electroporation effect within the electromagnetic field generated by the applicator 101. Electroporation may advantageously lead to increased cellular uptake of macromolecules within the electromagnetic field and thus may be of use when administering a pharmaceutical agent (i.e., immunotherapy or chemotherapy). For a variety of the various optional embodiments as have been discussed, the frequency of the radiofrequency signal driving the antenna is generally determined to be from about 434 megahertz to about 915 megahertz with the antennas and applicators designed to focus an electromagnetic field at a desired point underneath the skin of the patient (unless the tumor is a melanoma).

This may be optionally based upon the frequency transmitted from the signal generator, the power of the signal generator, the dielectromagnetic constant of the substrate used in the antenna, the configuration of the antenna, and additionally the material used to make the antenna. Optionally, the user also has the capacity to consider the various properties of the tissue to be treated in the patient so that the energy transferred to the patient is optimally used.

Furthermore, as previously discussed, a shield may be placed in the back layer to block radiation being reflected away from the tissue and thus both shield the healthcare provider while simultaneously providing more energy to the patient who is the intended recipient.

Further features of optional embodiments of the present invention may include a temperature control and sensor that may maintain the substrate (and therefore the skin adjacent the applicator) at or below a predetermined threshold temperature. In these optional embodiments, the temperature sensor may be placed centrally in the antenna although in other optional embodiments, the temperature sensor may be located at various locations upon the antenna which may in part be based upon the size of the applicator as well as the specific anatomical location for which the applicator will be used.

Optional aspects of the present invention may include a 50 ohm transmission line (i.e., connector cable 106) used with the medical apparatus and antenna though different transmission lines may be used depending upon the application, the desired applicator as well as what is needed for the patient. In one embodiment, the connector cable 106 is 4 feet long and has a cable loss of 0.129. In a preferred embodiment to be discussed with reference to FIGS. 3-5, a single cable is utilized between controller 100 and applicator 101 of similar length to improve reflectivity measurements and guarantee improved temperature control via a one wire temperature sensor and power delivery via power delivery circuit.

The antenna as used in optional embodiments of the present invention can often be described as a slot antenna which in optional embodiments may comprise a multi-patch slot antenna which can include a microstrip feed line oriented specific to the patch design. Yet in further embodiments the antenna can also be constructed as a single patch slot design and can include more patches depending upon the requirements of the usage scenario. In optional embodiments, the lower laminate can be described as a double slotted patch which is connected to the microstrip feed line and thus has connection to the connector cable.

Optional embodiments of the antenna can also include two substrate layers where a feed line is imprinted in silver on silicone of appropriate dielectromagnetics. A second layer of silicone may then be imprinted with the patch lens antenna. When such embodiments are placed together the effect is very similar to an antenna with multiple layers. In yet further optional embodiments, additional layers of patch slot combinations can be added to modify band width and to also alter the resonance frequency so that the energy field is changed. Furthermore, the applicator of the present invention can be optimized based in part upon tissue permittivity by adjusting the size of the patches, the slot as well, as the thickness of the used substrate.

Optional aspects of the present invention include the method of using the applicator for a variety of different ailments or reasons for the patient. One such optional use may be in the primary treatment of localized solid tumors. A similar but additional optional treatment may be in the adjuvant treatment of localized solid tumors in conjunction with either radiation or chemotherapy. Additionally this treatment may also include for lymphoid tumors which can optionally include loco-regional disease.

In additional optional aspects of the invention, the applicator may be used as an aid for in vivo electroporation with various pulse parameters. The applicator may be used to create a localized electromagnetic field as well as a localized thermal field.

Optional aspects of the invention may also include the capacity to include localized drug uptake within the region treated by the applicator. Additionally such treated region may optionally also experience tissue oxygenation as a result of the electromagnetic fields.

In yet further optional aspects of the present invention, applications may include for the improvement of wound healing by stimulating new collagen deposits as a result of the electromagnetic field created by the applicator.

FIG. 1 provides a general example of a display 140 of the medical apparatus. The display 140 is shown including its functional visual elements for the medical apparatus. In optional embodiments, the display 140 may be 420×270 pixels with 10×14 pixels for large characters and 8×10 pixels for small characters with 5 pixels being a minimum horizontal and 3 pixels per degree Celsius vertical. Other sizes and applications may be utilized.

In optional embodiments, a rotary encoder with a push to select switch may be located to the right of the display 140 or alternatively at different locations though in the proximity of the display 140 which may allow a user a selection of various treatment control functions within the display 140. In optional embodiments, there may be as many as five different panels across the bottom of the display 140 which can be selected and highlighted by the user.

In more optional embodiments, by rotating a rotary encoder, a user may move the selection of different panels and thus can provide both tactile feedback as well as visual feedback for each selection. Various options may be utilized to select different choices from a push to select activation to other embodiments known in the art.

In preferred embodiments, the display 140 may also provide a temperature time graph that presents temperature over a range that may be from about 10° to about 50° C. contrasted with a temperature at treatment time over a specific interval. Such interval may be from about 0 minutes to about 90 minutes though it can be shorter or longer depending on the specific application for the patient. The user may input a desired temperature limit into the system prior to treatment by accessing the temperature panel and thus, for example, in the provided FIG. 1 a limit of 39° C. is indicated by a straight horizontal line. The interval treatment time as displayed in the example is set at 45 minutes as indicated by the horizontal line at 45, the elapsed time being indicated as nine minutes. A history of the temperature measured at the applicator pad is superimposed on the temperature time graph 140, and thus this embodiment shows that the target temperature of about 39° C. was reached at approximately about 9 minutes after treatment began. The target temperature may be maintained by controlling the radiofrequency signal driving the applicator 101 over, for example, 36 minutes of treatment.

Delivery efficiency is indicative of the power transfer (see i.e., absorbed power) into the subcutaneous area of the patient adjacent the antenna (i.e., applicator 101) connected to the output of the medical apparatus. Thus, by maximizing subcutaneous heating, skin surface heating is minimized. This allows increased subcutaneous temperatures over prior art systems, providing a more effective therapy. Determining the delivery efficiency of the medical apparatus is made possible by use of the bidirectional coupler in a control unit of the medical apparatus to distinguish an output signal (i.e., the radiofrequency signal driving the applicator 101 and antenna) from a reflected signal.

Referring to FIG. 1, a medical apparatus 120 operable to induce localized hyperthermia 122 in a patient via an electromagnetic field emitted by an antenna connected to an output 302 of the medical apparatus 120 includes a control unit 100, the connector cable 106, and the applicator 101 including the antenna. Optionally, the applicator 101 includes the one or more temperature sensors 102, and the medical apparatus 120 further includes the temperature sensor cable 110 connecting the temperature sensor 102 to the control unit 100. As will be described with respect to FIGS. 3-5, having separate cables 106 and 110 for temperature sensing and radio frequency delivery may be preferably replaced with a single cable.

Figure 2:
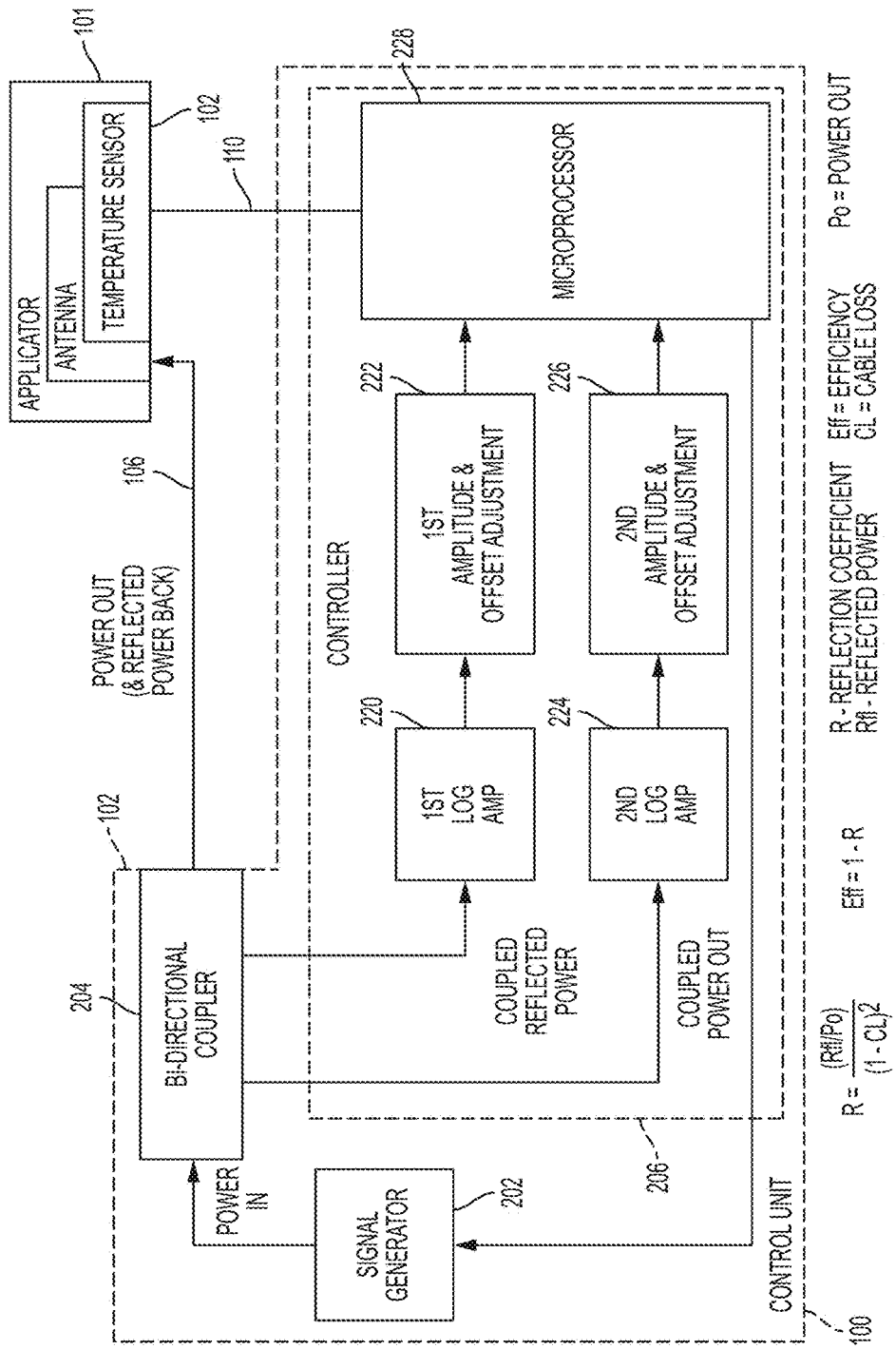
FIG. 2 is a schematic block diagram of the two cable hypothermia system of FIG. 1 showing its components comprising a signal generator 202, a bi-directional coupler 204, an output cable 106 for delivering radio frequency power and allowing reflected power to return to input/output 102 from antenna of applicator 101. Applicator 101 further may incorporate one or a plurality of temperature sensors 102 connected by second cable 110 to a microprocessor 228. The microprocessor receives coupled reflected power at log amplifier 220 which is processed by amplitude and offset adjustment 222. Also, coupled power out is fed to microprocessor 228 via a second log amp 224 and amplitude and offset adjustment 226 for processing by microprocessor 228 according to the equation depicted below. Moreover, one or more temperature sensors 102 provide temperature readings at the treatment site of applicator 101 vis a vis the patient so that the microprocessor may regulate signal generator 202 in regard to determined parameter values. For example, if the reflected power approaches power out, then, the applicator is not effective and the temperature reading of the at least one temperature sensor 102 should be low. The system may be turned off automatically until contact between the applicator 101 and the patient and treatment site are improved.

Referring to FIG. 2, the control unit 100 of the medical apparatus 120 of FIG. 15 includes a signal generator 202, a bidirectional coupler 204, and a controller 206. The control unit 100 also includes a power source (not shown) operable to provide power to components of the control unit 100 including to power the temperature sensor 102. One skilled in the art will understand that various power sources such as batteries and/or powerline power may be used to provide power to the components of the control unit 100 during operation.

The signal generator 202 is operable to generate radio frequency signal and provide the generated radiofrequency signal to the bidirectional coupler 204. The bidirectional coupler 204 is connected to the signal generator 202 and to the output 102 of the medical apparatus 120. In one embodiment, the output 102 of the medical apparatus 120 is synonymous with the output 102 of the bidirectional coupler 204 and with the output of the control unit 100. The bidirectional coupler 204 provides the radiofrequency signal generated by the signal generator 202 to the output 102 and receives a reflected signal from the applicator 101 (when impedances poorly match) at the output 102. Generally, the reflected signal is the signal reflected by the antenna of the applicator 101 via the connector cable 106.

The controller 206 is connected to the bidirectional coupler 204 and the signal generator 202. In one embodiment, the controller 206 is connected to the signal generator 202 via an input section of the bidirectional coupler 204 to receive the radio frequency signal. In another embodiment, the controller 206 is directly connected to the signal generator 202 to receive the radiofrequency signal directly from the signal generator 202. The controller 206 is operable to determine a power of the radiofrequency signal generated by the signal generator 202. The controller 206 also receives the reflected signal from the bidirectional coupler 204, and determines a power level of the reflected electromagnetic energy signal. The controller 206 then determines a delivery efficiency of the medical apparatus 120 as a function of the determined power of the radiofrequency signal generated by the signal generator 202 and the determined power of the reflected signal. In one embodiment, the delivery efficiency is determined by EQUATION 1.

$$DeliveryEfficiency = 1 - \frac{(Rfl/Po)}{(1-CL)^2} \quad \text{EQUATION 1}$$

Similarly, the controller 206 may determine the power absorbed by the localized area of the patient adjacent the applicator 100 via EQUATION 2.

$$AbsorbedPower = Po \times (1-CL) \times DeliveryEfficiency \quad \text{EQUATION 2}$$

In EQUATIONS 1 and 2, Rfl is the determined power of the reflected signal, Po is the determined power of the radiofrequency signal generated by the signal generator 202, and CL is a cable loss coefficient dependent on the connector cable 106. In one embodiment, the connector cable 106 is, for example, a 4 foot long coaxial 50 ohm transmission cable having a cable loss coefficient of 0.129.

In one embodiment, the display 140 is also connected to the controller 206. The controller 206 provides the determined delivery efficiency to the display 140, and the display 140 may display the delivery efficiency to a user (i.e., a caregiver or healthcare provider). It is contemplated that the user and patient may be one in the same under certain circumstances.

In one embodiment, the medical apparatus 120 also includes the at least one temperature sensor 102 of the applicator 101. The temperature sensor 102 measures a skin temperature of the patient adjacent the antenna of the applicator at the treatment site. For example, there may be three temperature sensors 102 forming a triangle about the antenna and a fourth temperature sensor may be directly embedded in a tumor and be wired or wirelessly connected to the applicator 102. That is, the temperature sensor 102 may, for example, be directly against the skin of the patient, or the temperature at the skin of the patient (i.e., the skin temperature of the patient) may be approximated as the temperature in the applicator 100 near the skin of the patient. The controller 206 may adjust an operating parameter of the signal generator 202 to reduce power delivered to the patient by the medical apparatus 120 in response to determining that the skin temperature exceeds a predetermined threshold (e.g., 39-42° C.).

One embodiment, the signal generator 202 generates the radio frequency signal as a function of operating parameters received from the controller 206. In this way, the controller 206 controls the signal generator 202 and the radiofrequency signal generated by the signal generator 202. The radiofrequency signal generated by the signal generator 202 may, for example, be a pulse width modulated signal having a base frequency between 400 and 460 MHz or between 890 and 950 MHz. The pulse width modulation may be between 1 and 10 Hz. That is, the pulse width modulation may be between one and 10 pulses per second (pps) or have a period of 0.1 seconds to 1 second. A duty cycle of the radiofrequency signal may vary between 0 and 100%. Thus, in one embodiment, the operating parameters provided to the signal generator 202 by the controller 206 may comprise a frequency, a power level, a duty cycle, and a number of pulses per second (i.e., period or pulse width modulation frequency). In one embodiment, the power level is variable from 2 to 40 Watts with therapy provided between 10 and 40 Watts (e.g., 10 Watts, 20 Watts, 30 Watts, or 40 Watts), and a 2 W mode of operation for adjusting the applicator 101 on the patient to maximize delivery efficiency. In one embodiment, the power level is adjusted by the controller 206 to maintain the skin temperature of the patient as determined via the temperature sensor 102 at a predetermined temperature (e.g., 39-42° C.).

In one embodiment, the controller 206 is operable to automatically optimize the operating parameters provided to the signal generator 202 in order to maximize delivery efficiency. The controller steps the radiofrequency signal through a plurality of operating parameters (e.g., sweeps the base frequency from 400 to 460 MHz in 10 MHz increment steps or sweeps the pulses per second from one pulse per second to 10 pulses per second in one pulse per second increment steps). The controller 206 determines the delivery efficiency at each of the plurality of operating parameters (e.g. at each base frequency step or pulses per second step). The controller 206 then determines the operating parameter of the plurality of operating parameters having the highest determined delivery efficiency. The controller 206 then controls the signal generator 202 to continue operation of the signal generator 202 at the operating parameter of the plurality of operating parameters determined to have the highest delivery efficiency. That is, the controller 206 selects the operating parameter resulting in the highest delivery efficiency and continues providing that operating parameter for the remainder of the hypothermia therapy session. The operating parameter may be, for example, the duty cycle, the power level, the frequency, or the pulses per second of the radiofrequency signal.

The controller 206 includes a first logarithmic amplifier 220, a first amplitude and offset compensation circuit 222, a second logarithmic amplifier 224, a second amplitude and offset compensation circuit 226, and a microprocessor 228. The first logarithmic amplifier 220 is connected to the bidirectional coupler 204 to receive the reflected signal from the bidirectional coupler 204 and provide an amplified reflected signal. The first amplitude and offset compensation circuit 222 is connected to the first logarithmic amplifier 220. The first amplitude and offset compensation circuit 222 receives the amplified reflected signal from the first logarithmic amplifier 220 and provides a digital representation of the power level of the reflected signal to the microprocessor 228. The second logarithmic amplifier 224 is connected to the signal generator 202 (either directly or via an input section of the bidirectional coupler 204). The second logarithmic amplifier 224 receives the radiofrequency signal from the signal generator 202 and provides an amplified radio frequency signal. The second amplitude and offset compensation circuit 226 is connected to the second logarithmic amplifier 224. The second amplitude and offset compensation circuit 226 receives the amplified radio frequency signal from the second logarithmic amplifier 224 and provides a digital representation of the power level of the radiofrequency signal (sent for application to a patient) to the microprocessor 228. The processor 228 is connected to the first amplitude and offset compensation circuit 222, to the second amplitude and offset compensation circuit 226, and to the at least one temperature sensor 102. The processor 228 may include input buffer circuitry to modify and digitize temperature signal level(s) received from the at least one temperature sensor 102. The processor 228 receives the digital representation of the reflected signal from the first amplitude and offset compensation circuit 222 and the digital representation of the radiofrequency signal from the second amplitude and offset compensation circuit 226. The processor 228 determines the delivery efficiency of the medical apparatus 120 based on the received digital representation of the reflected signal and the received digital representation of the radiofrequency signal according to the equations provided above.

A flowchart method of inducing localized hyperthermia in a patient via an electromagnetic field emitted by an antenna connected to an output (e.g., the output 102) of a medical apparatus (e.g., the medical apparatus 120) is disclosed with respect to the medical apparatus 120. The method begins with generating a radiofrequency signal via the signal generator 202 of the medical apparatus 120. The radiofrequency signal generated by the signal generator 202 is provided to the output 102 of the medical apparatus 120 via a bidirectional coupler 204 of the medical apparatus 120. Then, a reflected signal is received from the output 102 at the bidirectional coupler 204. Also, the generated radiofrequency signal from the signal generator 202 is received at the controller 206 of the medical apparatus 120. The controller 206 determines a power of the radiofrequency signal generated by the signal generator 202. Then, the reflected signal received at the controller 206 from the bidirectional coupler 204, and that 1714 the controller 1606 determines a power of the reflected signal. The controller 206 determines a delivery efficiency of the medical apparatus 1520 as a function of the determined power of the radiofrequency signal generated by the signal generator 202 and determines power of the reflected signal from the bidirectional coupler 204. As described above with respect to the medical apparatus 120, the method may optionally include automatically stepping through operating parameters of the signal generator 202 in order to optimize the delivery efficiency of the method.

As described above with respect to the medical apparatus 120, the controller 206 (especially processor 228) may determine the delivery efficiency of the medical apparatus 120 as a function of the determined power of the radiofrequency signal and the determined power of the reflected signal. To determine the delivery efficiency, the processor 228 determines a quotient of the reflected power divided by the power of the radiofrequency signal. The processor 228 also determines a difference of 1 minus a cable loss of the connector cable 106. The processor 228 then determines a square of the difference. The processor 228 determines a reflection coefficient by dividing the quotient by the square. Subtracting the reflection coefficient from 1 yields the delivery efficiency.

It is contemplated that the signal generator 202 and/or the bidirectional coupler 204 may be integral with the controller 206 within the scope of the claims. It is also contemplated that components of the controller 206 (e.g., the first logarithmic amplifier 220, the first amplitude and offset compensation circuit 222, the second logarithmic amplifier 224, and/or the second amplitude and offset compensation circuit 226) may be constructed integrally with the microprocessor 228 or in separate components.

Figure 3:
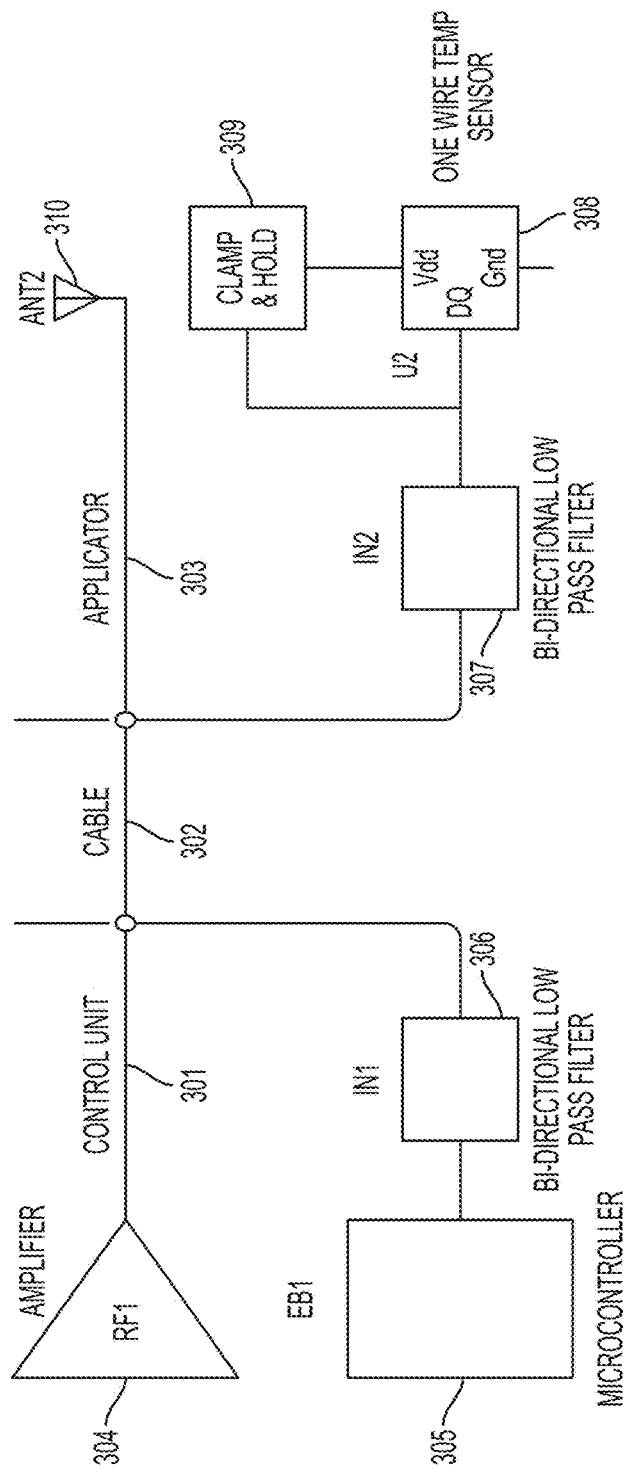
FIG. 3 provides an overview of the hypothermia treatment system modified so that only a single cable couples the control unit 100 and the applicator 101. In this modification, the microprocessor 228 may be a microcontroller 304 and the signal generator and bi-directional coupler may be an RFI amplifier 304 for outputting a desired RF signal via control unit 301 to single cable 302. Single cable 302 is shared by one wire temperature sensor 308 and by antenna 310 of application 101. Modified circuitry includes a first bi-directional low pass filter for powering the one wire temperature sensor and, for example, polling the sensor to output a low frequency data signal transmitted and passed by bi-directional low pass filters 307 and 306 to the microcontroller 305. Further features include a clamp and hold circuit 309 for the one wire temperature sensor providing a powering voltage Vdd where the one wire temperature sensor 308 further comprises a stable ground Gnd. The high power radio frequency signal is blocked from low pass filters 306 and 307 while the low frequency, low power polling, power and data signal indicating treatment site temperature is passed safely via the low pass filters to the microcontroller 305.
Figure 4:
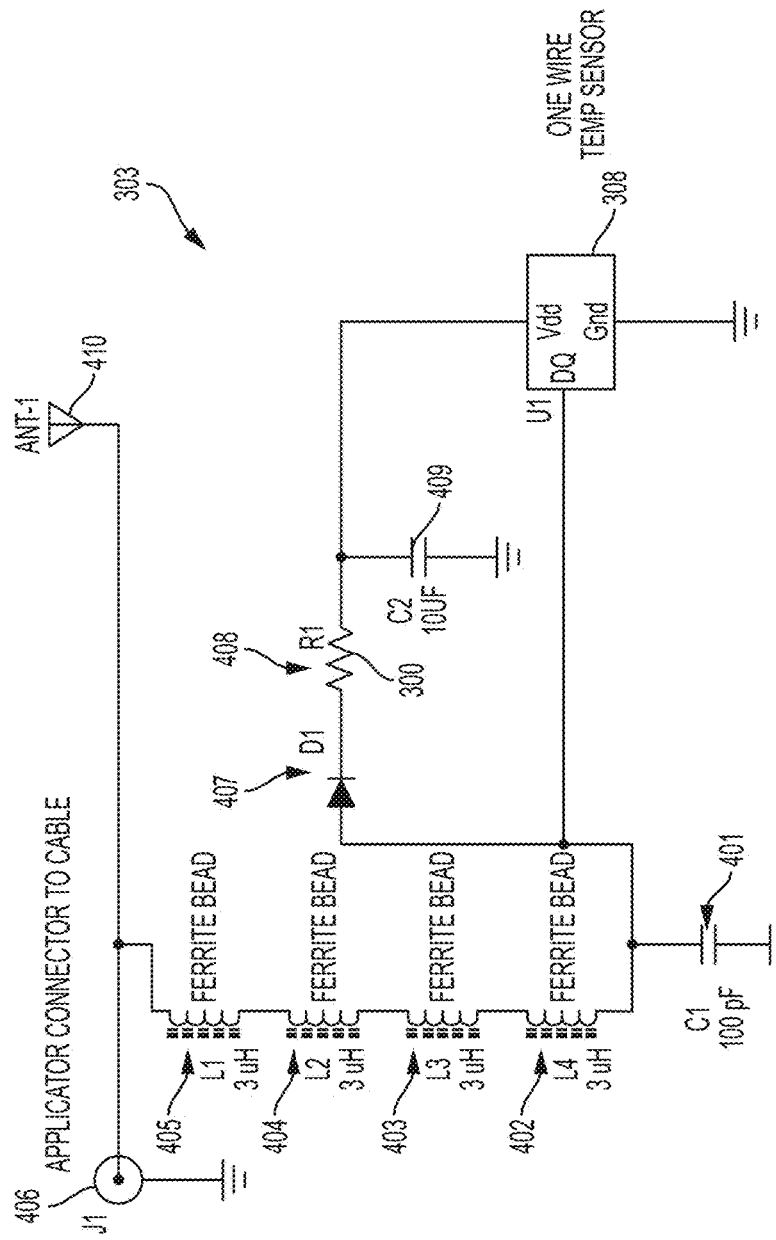
FIG. 4 provides details of electrical circuits at the applicator 101 end of FIG. 3.
Figure 5:
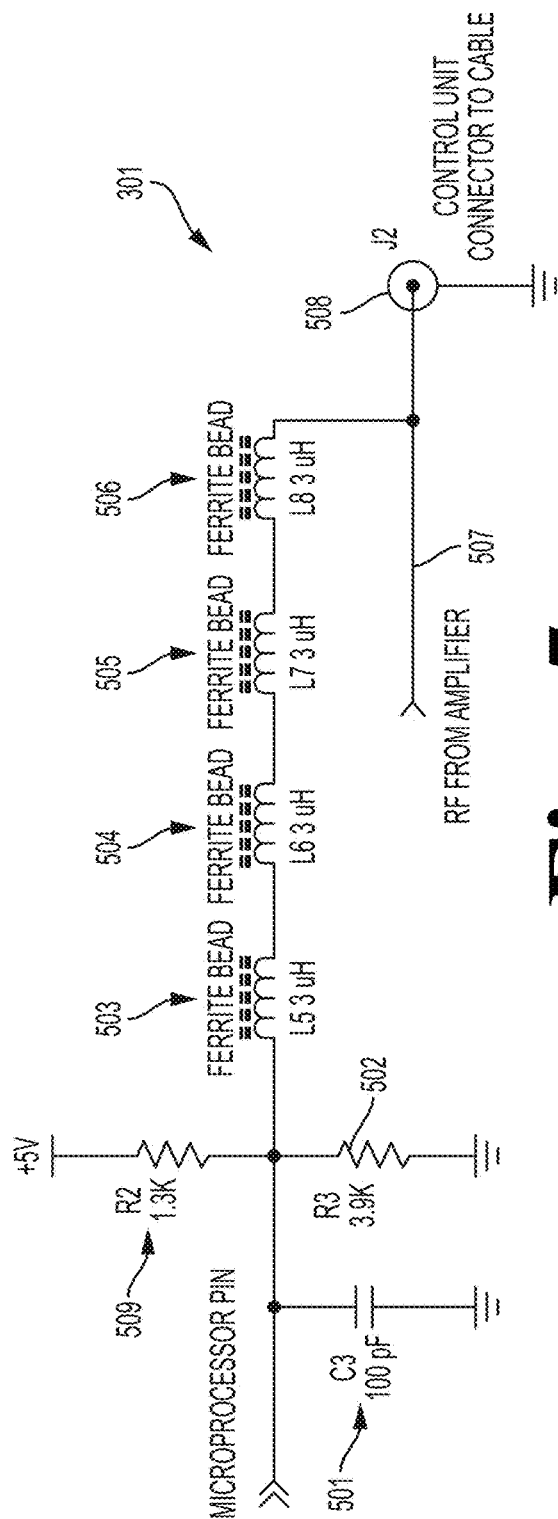
FIG. 5 provides details of electrical circuits at the control unit end where a microprocessor Pin (polling and power signal) is provided via the controller side low pass filter to the single cable and the temperature data is collected via the low pass filter. Meanwhile, the high power radio frequency signal is passed via single cable 507 to comprise the power/polling input/output 508 control unit connector to the single cable toward the applicator 101.

According to FIGS. 3-5, the two cable system is replaced by a single RF cable which also provides power to and low frequency poling of a one wire temperature sensor. In addition to transferring RF power to the applicator 101, the single RF cable provides an electrical path for monitoring and interrogating the one wire temperature sensor 308. Additional circuitry on the applicator 101 regenerates the operating voltage (Vdd) at the temperature sensor 308 thus eliminating an additional wire to supply this voltage. This change completely eliminates any problems associated with a faulty connection of the second temperature cable 110 and makes it easier to manipulate and adjust the applicator and improves the RF efficiency by eliminating a return path for RF energy through the former second temperature cable 110.

A block diagram which illustrates the components of the modified system is shown below in FIG. 5. The block diagram displayed in FIG. 3 is divided into two subsystems, a control unit subsystem 301 and an applicator sub system 303 connected by a single RF cable capable of carrying all frequencies including low frequency data signals and power. Within the control unit 301, the principal components which are relevant to this disclosure are: RF1 amplifier 304, an RF power source, EB1, supplying RF power to amplifier 304, a microprocessor 305 which supplies the low frequency control data for the at least one One Wire temperature sensor 308 and processes data originating at the one wire temperature sensor 308, and IN1 and IN2, bi-directional low pass filters 306 and 307 which prevent RF power from entering the microcontroller 305 but allows low frequency signaling data (temperature measurements, for example) to flow in either direction.

Within the applicator 101, more particularly, the components are: IN2, a bi-directional low pass filter 307 which blocks RF power from the at least one temperature sensor 308, a clamp and hold circuit 309 which extracts a DC voltage for supplying power to the at least one temperature sensor 308, and the at least one one wire temperature sensor 308 itself. In this single cable embodiment of the hypothermia treatment device, the temperature sensor 308 may be a DS1821 one wire temperature sensor (or equivalent sensor) manufactured by Maxim Integrated Circuits (previously by Dallas Semiconductor). However, the at least one temperature sensor 308 could be any One Wire temperature sensor in which control and output data are polled and carried by a single wire when polled at low frequency.

Note that the purpose of each of the two bi-directional low pass filters 306 and 307 (IN1 and IN2) is to act like an open circuit to RF energy, especially the high power electromagnetic energy signal for hypothermia treatment and is reflection and a short circuit to low frequency temperature sensor data signals. Thus, the combined functionality operates as if there are three physically separate lines; an RF power line (for treatment), A One Wire temperature sensor line and a sensor supply voltage line plus a common ground line. In the original two cable unit described by FIGS. 1 and 2, the temperature data, the supply voltage and the ground connection were carried by three separate wires within the temperature cable set.

Also note that the supply voltage for the temperature sensor 308 is generated on the applicator 101 and does not require a separate wire. From a theoretical viewpoint one might naively observe that this is nothing but frequency division multiplexing which has been used in communication systems for many years. In these systems, however, the power levels of the multiplexed components are roughly the same, and the components generally lie in the same common bandwidth whereas in the current situation of a hypothermia treatment system, there is a very large difference between the 20 to 30 watt RF signal for treatment and the very low (milliwatts) of power associated with the low frequency temperature data polling and returned temperature value signal. In addition, the temperature data is very low in frequency (for example, less than tens of kilobits per second) compared with the RF component which is on the order of 0.4 to 1.0 gHz.

FIG. 4 shows a specific implementation for the new circuitry present on the applicator and FIG. 5 shows a specific implementation for the additional circuitry required in the control unit.

Referring now to FIG. 4, there are shown, by way of example of a low pass filter, four ferrite beads, L1 405, L2 404, L3 403, and L4 402, each, for example, of a value of 3 millihenry in combination with a capacitor, C1 401 (for example, 100 pico-farads) which provide an example implementation of the low pass filter IN2 307 shown in FIG. 3 and a diode D1 407, resistor R1 408 and capacitor C2 409 (having a large value such as 10 microfarads) provide an example implementation of the clamp and hold circuit 309 shown in FIG. 3. Note that four ferrite beads may be used in this single cable implementation to provide a higher impedance than provided by a single bead and also to distribute any dissipated RF power so as not to overheat a single component of FIG. 4 (which might impact the temperature reading at at least one temperature sensor 308.

Referring now to FIG. 5, there are also shown a further set of four ferrite beads L5 (503), L6 (504), L7 (505) and L8 (506) each, for example, having a three milli-henry value. The four ferrite beads together with the capacitor C3 (again, 100 pico-farads for example) provide an example implementation of the bi-directional low pass filter IN1 shown in FIG. 3. R2 (for example, 1.3 kilo-Ohms and R3 (3.9 kilo-Ohms) divide, for example, a five volt supply voltage down to be compatible with the 3.5 volt microprocessor pin and the value of C3 at 100 pico-farads is chosen so as to be large enough to be an effective short circuit to RF but not so large that it interferes with the control signals to and from the microprocessor 305.

The single cable system of FIGS. 3-5 solves several problems that are present with the two cable system of FIGS. 1-2. First of all there is a reduction in clutter in the treatment area. This is important since the clinician must be constantly aware of the second cable and must deal with its presence when positioning the applicator 101. Certainly, the clinician, doctor, nurse or other user does not want to accidentally tangle the two cables.

Next the separate temperature cable provides an alternate path for RF energy in the two cable system. This causes several problems that are eliminated by using a single cable. When the temperature cable 110 is present, RF energy is reflected from the applicator 101 on both the RF cable 106 and the temperature cable 110. The portion that is reflected on the RF cable 106 can be measured and accounted for in computing the actual power that is delivered to the patient. The portion that is reflected on the temperature cable 110 cannot be measured and must be filtered out in the control unit 100 to prevent interference with the electronics. Thus, the single cable system provides a higher degree of accuracy in the measurement of the efficiency of operation and eliminates a source of stray "noise" inside the control unit 100.

Also, in the two cable system of FIGS. 1-2, energy is also coupled from the RF cable 106 to the temperature cable 110 all along their respective lengths. This occurs since it is impossible to completely shield the outside of the RF cable 106, and the near proximity of the temperature 110 cable provides a convenient "sink" for energy. This effect is exacerbated when the patient presents a large impedance mismatch due to inefficient positioning of the applicator 101, the inability to keep the applicator 101 in tight contact with the patient, or the presence of fur in animals, hair on a scalp, etc. In this case, the amount of energy that is coupled can be very large and has been known to burn the insulation on the temperature cable 110 if the two cables are allowed to touch one another. In order to minimize this effect in the two cable system, it is imperative that the clinician be constantly aware of the locations of the temperature cable 110 and the RF cable 106 and keep the two separated as much as possible, for example, by keeping them at a predetermined distance from one another (as telecommunications cables are separated from power cables on power/telephone poles.

Finally, the mechanical connection between the temperature cable 110 and the applicator 101 itself can cause large stresses to be transferred to the applicator 101 if the cable is bent at a sharp angle with respect to the applicator 101. These stresses have caused applicators of various shapes and sizes to be damaged and fail. In order to avoid this situation, it has also been necessary for the clinician to be constantly aware of the presence of the temperature cable 110 and how it is positioned.

Overall the single cable system is simpler, easier to use and presents a better clinical experience for the technician.

In yet further optional embodiments, various other settings may be utilized including wider or smaller temperature ranges as well as shorter or longer durations of time. By using these specific values for the sake of explaining the invention, applicants by no means intend to limit the applicants to the specific values previously described.

In even further optional embodiments of the control system for the applicator 101, faults may be reported through the system and handled by the medical apparatus. Generally the faults may include both hard and soft faults where hard faults are considered potentially harmful to the equipment which may in turn pose a threat to treatment whereas soft faults are expected occasionally and are generally not expected to be damaging or harmful to the equipment. As faults are expected to happen on occasion, the system may optionally be configured so as to report and provide information about the fault that may have occurred.

In yet further optional embodiments, the radio frequency parameters may be adjustable for a specific system. This may be controlled through the medical apparatus treatment settings and for example in some instances the frequency of the radiofrequency signal driving the applicator may be adjusted from 400 MHz to 460 MHz in 10 MHz steps. Similarly, power parameters may also be adjusted for the system and can include adjustments from about 2 watts to up to 40 watts. Various wattages may be utilized and the user can select specific wattages between the maximum and minimum wattage and in some instances increments in 10 watt steps may be utilized.

Furthermore, during treatment, various options may be adjustable including specific temperature (i.e., target temperature or maximum temperature) as well as the treatment time and other variables in between. Other options that may be adjusted in optional embodiments of the control system for the applicator 101 can include a change to the administration of the electromagnetic field from a constant output to a pulse width modulated arrangement and back and forth. In optional arrangements, pulse therapy (i.e., pulse width modulation) may be more beneficial to a user than a constant input from an electromagnetic field. As such, a user may change such feature throughout the treatment or prior to treatment and can adjust the length of pulse or the intensity. Alternatively, the medical apparatus may determine the mode of operation providing the highest delivery efficiency and automatically select that mode of operation.

In various embodiments of the present invention, the medical apparatus may include or be linked to a database which may be effective to store various parameters associated with a plurality of conditions, diseases, ailments or the like for which a user may want to provide treatment therefor. As such, the database may also store default settings for treatment associated with various patient species as well as conditions and may include specific regimens stored by the health care provider. Further optional embodiments may include a database that may be sorted to the specific patient so that the health care provider can create a template and/or specific program for a patient for an extended duration and maintain that template. In various optional embodiments, the applicator 101 may be used for a variety of different applications. These may include nosocomial infections also known as hospital acquired infections which can be associated with various microorganisms as well as bacteria. Other applications may include the treatment of diabetic foot ulcers. Other applications may include use for wound management and/or bed sores so as to alleviate pain experienced by a patient.

Further applications may include the system being used as an electronic contrast agent which can include uses for image technologies as previously mentioned.

Other ailments may also be affected through the use of the applicator of the present invention which can include skin conditions such as psoriasis, acne and cellulite.

Additional ailments which may be treated can include symptoms of Parkinson's disease where users may experience lessened effects of the neurological problems associated with Parkinson's through treatment.

Other applications may include the use of the system for sterilizing purposes for a dialysis machine.

Other muscle and joint disorders can be treated through the use of the medical apparatus of the present invention which include temporomandibular muscle and joint disorders as well as non-invasive forms of dialysis pain management for sports medicines. In other optional embodiments, including carpal tunnel syndrome and other painful musculoskeletal issues including lateral epicondylitis (tennis elbow), rotor cuff tears, meniscus tears, and trochanteric bursitis can be treated. Other applications can include the treatment of plantar fasciitis, chronic back pain, osteoarthritis, rheumatoid arthritis, gouty arthritis and even dysmenorrhea.

In yet further optional embodiments of the invention, while the applicator 101 has been described as being flexible, other forms of the applicator may include a cylindrical shape. Such a cylindrical shape may be used in instances where anatomical features cannot be properly treated with just a flat style applicator 101. Such optional embodiments with a cylindrical or elongated design may be used as a type of applicator for providing internal treatment which can include the insertion into various orifices on a patient. This can include and range from treatment options from cancer of the prostate to vaginal or cervical cancer as well as a potential treatment for various forms of colon cancer. Furthermore, the cylindrical shape can be designed so that the field permeates from one specific location upon the cylinder so that the electromagnetic field may be focused. However in optional embodiments, a variety of different antenna can be utilized with the cylindrical applicator and thus a user may choose the specific applicator that best suits the usage scenario.

As previously mentioned, aspects of optional embodiments of the present invention may include at least one temperature sensor and controller that may maintain the substrate (and thus the patient's skin adjacent the applicator) at a predetermined temperature. In these optional embodiments, the temperature control and sensor(s) may be placed centrally in the antenna although in other optional embodiments may be located at various locations upon or about the antenna or embedded in the tumor which may in part be based upon the size of the applicator 101 as well as the specific anatomical location for which the applicator will be used.

As also discussed, the antenna as used in the various optional embodiments of the present invention can often be described as a slot antenna which in optional embodiments may comprise a multi-patch slot antenna which can include a microstrip feed line oriented specific to the patch design. Yet in further embodiments, the antenna can also be constructed as a single patch slot design and yet further can include even more patches just depending upon the desires of the user. Furthermore, in optional embodiments the upper laminate can be described as a double slotted patch which is connected to the microstrip feed line and thus has connection to the coaxial cable.

Optional embodiments of the antenna can also include two substrate layers where a feed line is imprinted in silver on silicone of appropriate dielectromagnetics. A second layer of silicone may then be imprinted with the antenna. When such embodiments are placed together the effect is very similar to an antenna with multiple layers. In yet further optional embodiments, additional layers of patch slot combinations can be added to modify band width and to also alter the resonance frequency so that the electromagnetic field is changed for the specific application for the patient. Furthermore, the applicator 101 of the present invention can be optimized based in part upon tissue permittivity by adjusting the size of the patches the slot as well as the thickness of the used substrate.

As also has been discussed, optional aspects of the present invention include the method of using the applicator for a variety of different ailments or reasons for the patient. One such optional use may be in the primary treatment of localized solid tumors. A similar but additional optional treatment may be in the adjuvant treatment of localized solid tumors in conjunction with either radiation or chemotherapy. Additionally this treatment may also include for lymphoid tumors which can optionally include locoregional disease.

Further optional uses of the invention of the above-captioned application may be to improve local blood profusion including cutaneous and visceral perfusion.

In yet further optional aspects of the present invention applications may include for the improvement of wound healing by stimulating new collagen deposits as a result of the electromagnetic field created by the applicator.

Yet further optional aspects of the present invention may lead to increased local concentration of administered macromolecules. Otherwise stated this may include interaction with heavy metal compounds such as platinum chemotherapeutics which can lead to local drug concentrations. Increased concentration may be achieved in part through the accumulation of nanoparticles and drugs trapped based upon the physiologic charge of the moieties. Yet further such application may be used to increase the local tissue concentration of other charged moieties which may include antibiotics or DNA/RNA nucleotides which may be used in gene therapeutics.

Yet even further optional aspects of the present invention may be used for the purpose of the adjuvant treatment of osteoarthritis as well as the adjuvant treatment of neurogenetic pain, adjuvant treatment of musculoskeletal pain and additionally may be used to improve tendon healing or tissue perfusion prior to exercise.

In yet additional optional aspects of the present invention, the medical apparatus may be used to provide an electromagnetic field that can be used as a non-invasive contrast agent to assist in ultrasound and MRI imaging. Similarly, the electromagnetic field generated by the antenna can be used as a contrast agent to assist in detection of inflammatory neoplastic or degenerative lesions.

In further optional embodiments of the present invention the medical apparatus may be associated with software residing on either a computer or network. Generally a host system may be utilized with the present invention and may include one or more data processors as well as a graphic user interface computer readable memory containing a computer program executable by one or more data processors using techniques as are well known in the art. In some embodiments a single membrane medium may be provided which is effective to store software useful for the applicator and any data which is received in relation to the program. In other embodiments a plurality of memory media including that containing the computer program as well as one or more databases or equivalent storage entities may be provided and functionally linked to collectively perform the functions of the system as described herein.

As described briefly with regard to the optional software aspects of the invention, various controls and operating parameters can be used for treating a patient. In many optional embodiments, power output may be controlled automatically through feedback from the antenna temperature sensor and feedback from the applicator. Such design can allow for maximal power during the initial heating and a reduction to near zero at or above the desired target temperature.

Yet furthermore, optional aspects may further include a pulse feature where one could tailor pulse repetitions or pulse width in duty cycle which can in part be based upon feedback from the temperature sensor to the control unit. For example, during the initial heating of the patient, the intervals can be shortened so as to speed up acquisition of a preset target temperature. Subsequently, at the desired temperature the values can be adjusted to maintain a constant surface temperature.

For various applications for species of animals with tumors that may be considered stage 3 or higher, often eight to twelve treatments using the medical apparatus of the present invention may be necessary to provide treatment. General treatment times for a localized region range from about 20 minutes to about 40 minutes though can be shorter or longer. Often the time to reach a surface temperature of greater than or equal to 39 degrees Celcius range from about six minutes to about 15 minutes though could be longer or shorter. Time to reach a optionally considered maximum temperature can range from about eight minutes to about twenty-three minutes. Obviously these times can be longer or shorter and not meant to be limiting upon the invention. Rather, they are provided as possible ranges and variants for treatment.

In administering hyperthermic treatment by way of the inventive applicator, response times range from about one week to eight weeks, with averages possibly being around four and one half week or so for some animals. In some patients, a complete response may be seen whereas in other patients there may be a temporary delay or slowing of the tumor growth.

Advantageously the medical apparatus of the present invention may preclude the use of a water bolus as the skin of a patient remains cooler than prior art designs. Otherwise stated, the applicators as disclosed herein may focus the energy transmission and thus not require the increased voltage as does prior art devices and therefore is less likely to burn a patient's skin. Thus, an optional aspect of the invention is a use of an applicator without a water bolus for treatment of a patient.

Furthermore, sizes of various structural parts and materials used to make the above mentioned components are illustrative and exemplary only, and persons of ordinary skill in the art would recognize that these sizes and materials can be changed as necessary to produce different results or different desired characteristics.

It will be understood by those of skill in the art that information and signals may be represented using any of a variety of different technologies and techniques (e.g., data, instructions, commands, information, signals, bits, symbols, and chips may be represented by voltages, currents, electromagnetic waves, magnetic fields or particles, optical fields or particles, or any combination thereof). Likewise, the various illustrative logical blocks, modules, circuits, and algorithm steps described herein may be implemented as electronic hardware, computer software, or combinations of both, depending on the application and functionality. Moreover, the various logical blocks, modules, and circuits described herein may be implemented or performed with a general purpose processor (e.g., microprocessor, conventional processor, controller, microcontroller, state machine or combination of computing devices), a digital signal processor ("DSP"), an application specific integrated circuit ("ASIC"), a field programmable gate array ("FPGA") or other programmable logic device, discrete gate or transistor logic, discrete hardware components, or any combination thereof designed to perform the functions described herein. Similarly, steps of a method or process described herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. Although embodiments of the present invention have been described in detail, it will be understood by those skilled in the art that various modifications can be made therein without departing from the spirit and scope of the invention as set forth in the appended claims.

A controller, processor, computing device, client computing device or computer, such as described herein, includes at least one or more processors or processing units and a system memory. The controller may also include at least some form of computer readable media. By way of example and not limitation, computer readable media may include computer storage media and communication media. Computer readable storage media may include volatile and nonvolatile, removable and non-removable media implemented in any method or technology that enables storage of information, such as computer readable instructions, data structures, program modules, or other data. Communication media may embody computer readable instructions, data structures, program modules, or other data in a modulated data signal such as a carrier wave or other transport mechanism and include any information delivery media. Those skilled in the art should be familiar with the modulated data signal, which has one or more of its characteristics set or changed in such a manner as to encode information in the signal. Combinations of any of the above are also included within the scope of computer readable media.

This written description uses examples to disclose the invention and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

It will be understood that the particular embodiments described herein are shown by way of illustration and not as limitations of the invention. The principal features of this invention may be employed in various embodiments without departing from the scope of the invention. Those of ordinary skill in the art will recognize numerous equivalents to the specific procedures described herein. Such equivalents are considered to be within the scope of this invention and are covered by the claims.

All of the compositions and/or methods disclosed and claimed herein may be made and/or executed without undue experimentation in light of the present disclosure. While the compositions and methods of this invention have been described in terms of the embodiments included herein, it will be apparent to those of ordinary skill in the art that variations may be applied to the compositions and/or methods and in the steps or in the sequence of steps of the method described herein without departing from the concept, spirit, and scope of the invention. All such similar substitutes and modifications apparent to those skilled in the art are deemed to be within the spirit, scope, and concept of the invention as defined by the appended claims.

Thus, although there have been described particular embodiments of the present invention of a new and useful SINGLE CABLE APPARATUS AND METHOD FOR HYPERTHERMIC TREATMENTS it is not intended that such references be construed as limitations upon the scope of this invention except as set forth in the following claims.

What is claimed is:

1. A single cable medical apparatus adapted to induce localized hyperthermia in a patient via an electromagnetic field emitted by an antenna connected to an output of the medical apparatus, said medical apparatus comprising:
  a signal generator operable to generate a radio frequency signal for delivery via a single cable to an applicator;
  a bidirectional coupler connected to the signal generator and to the output of the medical apparatus, wherein the bidirectional coupler is operable to provide the radio frequency signal generated by the signal generator to the output and to receive a reflected signal from the output to the single cable;
  first and second low pass filters, a first low pass filter connected to a microprocessor and a second low pass filter connected to a temperature sensor, the first and low pass filters for passing a low frequency temperature polling and temperature data signal and blocking the radio frequency signal generated by the signal generator and its reflection, and
  a clamp and hold circuit at an applicator end of the single cable, the clamp and hold circuit coupled between the second low pass filter and the temperature sensor.

2. The medical apparatus of claim 1, each low pass filter comprising a plurality of ferrite beads and a capacitor, the low pass filters for blocking the radio frequency signal from reaching the temperature sensor.

3. The medical apparatus of claim 1, the clamp and hold circuit comprising a diode connected in series with a resistor and in parallel with a capacitor having a value sufficiently high to provide voltage to the temperature sensor and sustain a low frequency temperature data polling rate.

4. The medical apparatus of claim 3, the single cable providing polling of the temperature sensor to obtain temperature data at a treatment site.

5. The medical apparatus of claim 1, further comprising a controller, wherein the signal generator is operable to generate the radio frequency signal as a function of an operating parameter provided by the controller, wherein the operating parameter is a frequency, a power level, a duty cycle, or a pulses per second of the radio frequency signal.

6. The medical apparatus of claim 5, wherein the signal generator is operable to generate the radio frequency signal as a function of an operating parameter provided by the controller, the controller is operable to control the signal generator by providing the operating parameter to the signal generator, and wherein the controller is further operable to:
  step the radio frequency signal through a plurality of operating parameters;
  determine a delivery efficiency of the radio frequency signal while the radio frequency signal is at each of the plurality of operating parameters; and
  determine the operating parameter of the plurality of operating parameters having the highest delivery efficiency; and
  control the signal generator to continue operation of the signal generator at the operating parameter of the plurality of operating parameters determined to have the highest delivery efficiency.

7. The medical apparatus of claim 6, wherein the operating parameter is a duty cycle, a power level, a frequency, or a pulses per second of the radio frequency signal.

8. The medical apparatus of claim 6, wherein the signal generator is operable to generate the radio frequency signal as a function of a frequency provided by the controller, the controller is operable to control the signal generator by providing the frequency to the signal generator, and wherein the controller is further operable to:
  step the radio frequency signal through a plurality of different frequencies;
  determine the delivery efficiency while the radio frequency signal is at each of the plurality of frequencies; and
  determine the frequency of the plurality of frequencies having the highest delivery efficiency; and
  control the signal generator to continue operation of the signal generator at the frequency of the plurality of frequencies determined to have the highest delivery efficiency.

9. The medical apparatus of claim 6, wherein the controller comprises:
  a first logarithmic amplifier connected to the bidirectional coupler, wherein the first logarithmic amplifier is operable to receive the reflected signal from the bidirectional coupler and provide an amplified reflected signal;
  a first amplitude and offset compensation circuit connected to the first logarithmic amplifier, wherein the first amplitude and offset compensation circuit is operable to receive the amplified reflected signal from the first logarithmic amplifier and provide a digital representation of the reflected signal;
a second logarithmic amplifier connected to the signal generator, wherein the second logarithmic amplifier is operable to receive the radio frequency signal from the signal generator and provide an amplified radio frequency signal;
a second amplitude and offset compensation circuit connected to the second logarithmic amplifier, wherein the second amplitude and offset compensation circuit is operable to receive the amplified radio frequency signal from the second logarithmic amplifier and provide a digital representation of the radio frequency signal;
a processor connected to the first amplitude and offset compensation circuit and to the second amplitude and offset compensation circuit, wherein the processor is operable to:
receive the digital representation of the reflected signal;
receive the digital representation of the radio frequency signal; and
determine the delivery efficiency of the medical apparatus based on the received digital representation of the reflected signal and the received digital representation of the radio frequency signal.

10. The medical apparatus of claim 6, wherein the signal generator is operable to generate the radio frequency signal as a function of a pulses per second provided by the controller, the controller is operable to control the signal generator by providing the pulses per second to the signal generator, and wherein the controller is further operable to:
step the radio frequency signal through a plurality of different pulses per second;
determine the delivery efficiency while the radio frequency signal is at each of the plurality of pulses per second; and
determine the pulses per second of the plurality of pulses per second having the highest delivery efficiency; and
control the signal generator to continue operation of the signal generator at the pulses per second of the plurality of pulses per second determined to have the highest delivery efficiency.

11. The medical apparatus of claim 6, the applicator having an antenna adapted to induce a localized hypothermia at a treatment site of the patient via the generated radio frequency signal comprising an electromagnetic field output emitted by the antenna, the antenna being connected to the output of the medical apparatus, the medical apparatus further comprising the controller for determining a power of the radio frequency signal and the antenna for receiving the reflected signal for analysis by the controller.

12. The medical apparatus of claim 11 further comprising:
a display for providing an output of the controller comprising a determined delivery efficiency of the electromagnetic field output of the antenna of the medical apparatus and displaying the determined delivery efficiency of the electromagnetic field output of the antenna to a user of the medical apparatus.

13. The medical apparatus of claim 11, the controller, responsive to the signal generator generating the radio frequency signal, determining a duty cycle for the radio frequency signal.

14. The medical apparatus of claim 11, the controller for determining a quotient of reflected signal power divided by power of the radio frequency signal and determining u reflection coefficient from the reflected signal power.

15. The medical apparatus of claim 11, the applicator comprising a plurality of layers, the lowest layer being a high impedance substrate layer adapted to permit the antenna to be flexible and for impedance matching of the applicator to the treatment site.

16. The medical apparatus of claim 15, the high impedance substrate layer adapted to make flexible contact with a treatment site of the patient.

17. The medical apparatus of claim 5, further comprising:
a temperature sensor connected to the controller adapted to measure a skin temperature of the patient, the temperature sensor incorporated into the applicator.

18. The medical apparatus of claim 1, further comprising an applicator, wherein the applicator comprises the antenna, and the single cable combines a connector cable and a temperature sensor cable into the single cable and is operable to connect the antenna in the applicator to the output.

19. The medical apparatus of claim 1, the applicator comprising a layer forming a slot antenna comprising a printed circuit board.

20. The medical apparatus of claim 19, the slot antenna having an aperture measuring between thirty-five and forty-five square centimeters.

* * * * *